(12) United States Patent
Chan

(10) Patent No.: US 10,159,669 B2
(45) Date of Patent: Dec. 25, 2018

(54) INDIVIDUAL AND COMBINATION OF MDIVI-1 AND NUTLIN-3 FOR TOPICAL OR INTRAVITREAL OPHTHALMIC USE

(76) Inventor: Ian H. Chan, Bayside, NY (US)

( * ) Notice: Subject to any disclaimer, the term of this patent is extended or adjusted under 35 U.S.C. 154(b) by 847 days.

(21) Appl. No.: 12/715,384

(22) Filed: Mar. 2, 2010

(65) Prior Publication Data

US 2011/0218206 A1  Sep. 8, 2011

(51) Int. Cl.
*A61K 31/496* (2006.01)
*A61K 31/517* (2006.01)

(52) U.S. Cl.
CPC .......... *A61K 31/496* (2013.01); *A61K 31/517* (2013.01)

(58) Field of Classification Search
CPC .............................. A61K 31/496; A61K 31/517
See application file for complete search history.

(56) References Cited

U.S. PATENT DOCUMENTS

| | | | | |
|---|---|---|---|---|
| 6,617,346 B1 * | 9/2003 | Kong | ................... | C07D 233/20 514/399 |
| 6,734,302 B2 * | 5/2004 | Kong | ................... | C07D 233/22 544/139 |
| 6,916,833 B2 * | 7/2005 | Kim | ..................... | C07D 211/52 514/328 |
| 7,060,713 B2 * | 6/2006 | Kim | ..................... | C07D 211/52 514/328 |
| 7,425,638 B2 * | 9/2008 | Haley | .................. | C07D 233/22 548/334.1 |
| 7,579,368 B2 * | 8/2009 | Fotouhi | ................ | C07D 233/22 514/385 |
| 7,625,895 B2 * | 12/2009 | Dominique | .......... | C07D 471/04 514/235.8 |
| 2005/0038051 A1 * | 2/2005 | Nunnari | ............... | C07D 239/95 514/266.2 |
| 2008/0287473 A1 * | 11/2008 | Nunnari | ............... | C07D 239/95 514/266.3 |

* cited by examiner

*Primary Examiner* — Zohreh A Fay
(74) *Attorney, Agent, or Firm* — Duane Morris LLP

(57) ABSTRACT

Disclosed are pharmaceutical compositions comprising mdivi-1 and nutlin-3, individually and in combination, for topical or intravitreal ophthalmic delivery and a method of treatment comprising administering said composition when indicated for glaucoma, optic neuropathies including Leber Hereditary Optic Neuropathy, arteritic or non-arteritic Ischemic Optic Neuropathy, and retinal artery and vein occlusions.

9 Claims, No Drawings

INDIVIDUAL AND COMBINATION OF MDIVI-1 AND NUTLIN-3 FOR TOPICAL OR INTRAVITREAL OPHTHALMIC USE

BACKGROUND OF THE INVENTION

This invention relates to the topical and/or intravitreal ophthalmic use of mdivi-1 and nutlin-3, individually or in combination, when indicated for treatment of glaucoma, ischemic optic neuropathies, hereditary optic neuropathies and retinal artery and vein occlusions.

Nutlin-3 is disclosed in U.S. Pat. Nos. 6,617,346, 6,734,302, 6,916,833, 7,060,713, 7,425,638, 7,579,368, 7,625,895. The claims of the listed patents describe nutlin-3 inhibition of the interaction of MDM2 protein with a p53-like peptide and hence have anti proliferative activity. In this invention, nutlin-3 inhibit apoptosis by inhibiting Bax and Bak in the apoptosis pathway and produce neuroprotective effects rather than induce apoptosis as claimed in the previous patent disclosures.

mdivi-1 is disclosed in U.S. Pat. Application No. 20050038051 and 20080287473. The claims of the listed patents describe mdivi-1 regulation of apoptosis via regulating mitochondrial fission or fusion.

This patent claims nutlin-3 and mdivi-1 as an ophthalmic drug. In combination, these drugs block Bax/Bak and Drp1 interaction on the mitochondria surface as a key step in the apoptotic pathway of various ophthalmic diseases including glaucoma, ischemic optic neuropathy, hereditary optic neuropathy and retinal artery/vein occlusions.

DESCRIPTION

Nutlin-3 is represented by the chemical formulae (I) and (II) depicted below described in U.S. Pat. Nos. 6,617,346, 6,743,302, 6,916,833, 7,060,713, 7,425,638, 7,579,368, 7,625,895.

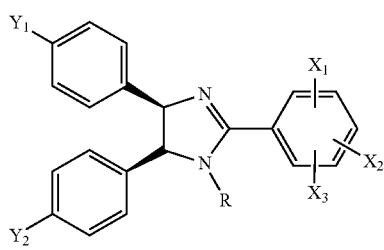

(I)

wherein R is —C═$OR_1$,
wherein $R_1$ is C1-C4 alkyl, —C═CHCOOH, —$NHCH_2CH_2R_2$, —$N(CH_2CH_2OH)CH_2CH_2OH$, —$N(CH_3)CH_2CH_2NCH_3$, —$N(CH_3)CH_2CH_2N(CH_3)CH_3$, saturated 4-, 5- and 6-membered rings, saturated and unsaturated 5- and 6-membered rings containing at least one hetero atom wherein the hetero atom is selected from S, N and O and being optionally substituted with a group selected from lower alkyl, —C═O—$R_5$, —OH, lower alkyl substituted with hydroxy, lower alkyl substituted with —$NH_2$, N-lower alkyl, —$SO_2CH_3$, ═O, —$CH_2C$═$OCH_3$, and 5- and 6-membered saturated rings containing at least one hetero atom selected from S, N and O,
wherein $R_5$ is selected from H, lower alkyl, —$NH_2$, —N-lower alkyl, lower alkyl substituted with hydroxy, and lower alkyl substituted with $NH_2$,
wherein $R_2$ is selected from —$N(CH_3)CH_3$, —$NHCH_2CH_2NH_2$, —$NH_2$, morpholinyl and piperazinyl,
$X_1$, $X_2$ and $X_3$ are independently selected from —OH, C1-C2 alkyl, C1-C5 alkoxy, —Cl, —Br, —F, —$CH_2OCH_3$, and —$CH_2OCH_2CH_3$,
or one of $X_1$, $X_2$ or $X_3$ is H and the other two are independently selected from hydroxy, lower alkyl, lower alkoxy, Cl, Br, F, $CF_3$—$CH_2OCH_3$, —$CH_2OCH_2CH_3$—$OCH_2CH_2R_3$, —$OCH_2CF_3$, and —O—$R_4$,
or one of $X_1$, $X_2$ or $X_3$ is H and the other two taken together with the two carbon atoms and the bonds between them from the benzene ring to which they are substituted form a 6-membered saturated ring that contains at least one hetero atom selected from S, N, and O,
wherein $R_3$ is selected from —F, —$OCH_3$, —$N(CH_3)CH_3$, unsaturated 5-membered rings containing at least one hetero atom wherein the hetero atom is selected from S, N and O,
wherein $R_4$ is a 3- to 5-membered saturated ring and
$Y_1$ and $Y_2$ are each independently selected from —Cl, —Br, —$NO_2$, —C≡N and —C≡CH.

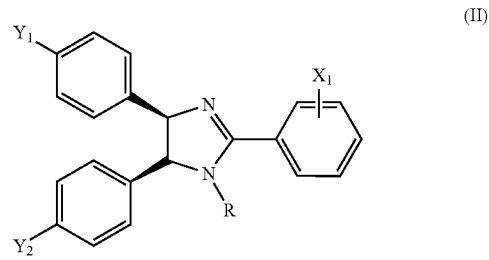

(II)

wherein R is —C═$OR_1$,
wherein $R_1$ is selected from C1-C4 alkyl, saturated 5- and 6-membered rings, saturated 5- and 6-membered rings containing at least one hetero atom wherein the hetero atom is selected from S, N and O and being optionally substituted with a group selected from C1-C2 alkyl, C1-C3 alcohol, —$N(CH_3)CH_3$, and —C═$OCH_3$, and 5- and 6-membered rings containing at least one hetero atom wherein the hetero atom is selected from S, N, and O,
$X_4$ is selected from C1-C2 alkyl, C1-C5 alkoxy, —Cl, —Br, —F, —$OCH_2C$═OOQ, —$OCH_2$ cyclopentyl, —$CH_2OCH_2$-phenyl, saturated and unsaturated 5- and 6-membered rings, saturated and unsaturated 5- and 6-membered rings containing at least one hetero atom wherein the hetero atom is selected from S, N and O,
wherein Q is selected from H and lower alkyl,
$Y_1$ and $Y_2$ are independently selected from —Cl, —Br, —$NO_2$, —C≡N and —C≡CH,
with the proviso that where $Y_1$ and $Y_2$ are both —Cl, and $R_1$ is —$CH_3$ or phenyl, then $X_4$ is not —Cl.

Mdivi-1 is represented by the chemical formula (III) depicted below described in U.S. Pat. Application No. 20050038051 and 20080287473.

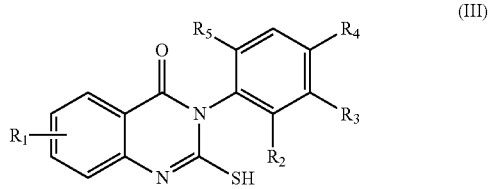

(III)

wherein $R_1$ is independently H; a C1-C18 alkyl, which may be branched, may contain a heteroatom or may be substituted, or combinations thereof; a C1-C18 alkenyl, which may be branched, may contain a heteroatom or may be substituted, or combinations thereof; a C1-C18 alkynl, which may be branched, may contain a heteroatom or may be substituted, or combinations thereof; a C3-C18 aryl which may contain a side group, may contain a bridge, may contain a heteroatom or may be substituted, or combinations thereof; or a C5-C18 cycloalkyl which may contain a side group, may contain a bridge, may contain a heteroatom or may be substituted, or combinations thereof;

$R_2$ is H; a C1-C18 alkyl, which may be branched, may contain a heteroatom or may be substituted, or combinations thereof; or a halogen;

$R_3$ is H; a C1-C18 alkyl, which may be branched, may contain a heteroatom or may be substituted, or combinations thereof;

$R_4$ is H or a halogen; and $R_5$ is H or a halogen, with the provisos that when $R_3$ is H and $R_4$ is H or a halogen, $R_5$ is a halogen, or when $R_2$ is a halogen $R_5$ is H or a halogen.

Nutlin-3 and its active emantiomer nutlin-3a are available from Roche, Inc and Cayman Chemical, Inc. Mdivi-1 is available from various sources, including Enzo Life Science.

The compositions of the present invention are administered either topically or intravitreally. The dosage is 0.001 to 1.0, e.g. mg/per eye BID to QID or as 1 time dose; wherein the cited mass figures represent the sum of the two components, mdivi-1 and nutlin-3. The compositions of the present invention can be administered as solutions in a suitable ophthalmic vehicle.

The precise regimen is left to the discretion of the clinician, it is recommended that the solution be topically applied by placing one drop in each eye once to four times a day or as one time or weekly intravitreal injections. Other ingredients which may be desirable to use in the ophthalmic preparations of the present invention include preservatives, co-solvents and viscosity building agents.

Antimicrobial Preservative

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. In the prior art ophthalmic products, typically such preservatives are employed at a level of from 0.004% to 0.02%. In the compositions of the present application the preservative, preferably benzalkonium chloride, may be employed at a level of from 0.001% to less than 0.01%, e.g. from 0.001% to 0.008%, preferably about 0.005% by weight. It has been found that a concentration of benzalkonium chloride of 0.005% is sufficient to preserve the compositions of the present invention from microbial attack. This concentration may be advantageously compared to the requirement of 0.01% benzalkonium chloride to preserve mdivi-1 and nutlin-3 in the individual, commercially-available ophthalmic products. It is noted that it is known that benzalkonium chloride at high concentrations is cytotoxic. Therefore, minimizing the patient's exposure to benzalkonium chloride, while providing the preservative effects afforded by benzalkonium chloride, is clearly desirable.

Co-Solvents

The solubility of the components of the present compositions may be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Typically such co-solvents are employed at a level of from 0.01% to 2% by weight.

Viscosity Agents

Viscosity increased above that of simple aqueous solutions may be desirable to increase ocular absorption of the active compound, to decrease variability in dispensing the formulation, to decrease physical separation of components of a suspension or emulsion of the formulation and/or to otherwise improve the ophthalmic formulation. Such viscosity building agents include as examples polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art. Such agents are typically employed at a level of from 0.01% to 2% by weight.

The present invention further comprises an article of manufacture comprising packaging material and a pharmaceutical agent contained within said packaging material, wherein the pharmaceutical agent is therapeutically effective for neuroprotection and wherein the packaging material comprises a label which indicates the pharmaceutical agent can be used for lowering intraocular pressure and wherein said pharmaceutical agent comprises an effective amount of mdivi-1 and an effective amount of nutlin-3.

The following example is a representative pharmaceutical composition of the invention for topical use when indicated for treating glaucoma, ischemic optic neuropathy, hereditary optic neuropathy and retinal artery or vein occlusion.

Example I

The combination of active pharmaceutical ingredients is as follows: mdivi-1 0.10% (w/v) and nutlin-3 Maleate 0.25% (w/v).

The formulation vehicle contains an isotonic phosphate buffer system at pH 6.9. The formulation preservative is benzalalkonium chloride (BAK) at a concentration of 0.005% (w/v) (50 ppm).

The invention has been described herein by reference to certain preferred embodiments. However, as obvious variations thereon will become apparent to those skilled in the art, the invention is not to be considered as limited thereto.

A1. A method of treating glaucoma, ischemic optic neuropathy or retinal artery or vein occlusion by topical or intravitreal administration of nutlin-3, including the active enantiomer nutlin-3a, to an eye of a person in need once to four times a day or as one time or weekly intravitreal injections as the sole active agent.

A2. A method of treating glaucoma, ischemic optic neuropathy or retinal artery or vein occlusion by topical or intravitreal administration of mdivi-1 to an eye of a person in need once to four times a day or as one time or weekly intravitreal injections as the sole active agent.

A3. A method of treating glaucoma, ischemic optic neuropathy or retinal artery or vein occlusion by topical administration of nutlin-3 (including the active enantiomer nutlin-3a) to an eye of a person in need thereof, said improvement comprising topically administering to said eye, in a single composition, nutlin-3 and mdivi-1 once to four times a day topically or as one time or weekly intravitreal injections; as the sole active agents; wherein said method is as effective as administration of nutlin-3 once to four times a day and mdivi-1 once to four times a day or as one time or weekly intravitreal injections to said eye, herein the two compounds are administered in separate compositions.

What is claimed is:

1. A method of treating ischemic optic neuropathy in an eye of a person in need thereof, the method comprising administering, to the person, a composition comprising a therapeutically effective amount of nutlin-3 or nutlin-3a.

2. The method of claim 1, wherein the composition is administered to said person once to four times per day.

3. The method of claim 1, wherein the composition is administered once per week.

4. The method of claim 1, wherein the composition is administered once.

5. The method of claim 1, wherein the composition is formulated for intravitreal injection or topical delivery.

6. The method of claim 5, wherein the composition is formulated for intravitreal injection.

7. The method of claim 1, wherein the composition further comprises a preservative.

8. The method of claim 7, wherein the preservative is less than 0.005 wt. %.

9. The method of claim 7, wherein the preservative is benzalkonium chloride.

* * * * *